US00PP25236P2

(12) United States Plant Patent
Graff

(10) Patent No.: US PP25,236 P2
(45) Date of Patent: Jan. 20, 2015

(54) ***HIBISCUS* PLANT NAMED 'JUNO'**

(50) Latin Name: *Hibiscus rosa-sinensis*
Varietal Denomination: Juno

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 182 days.

(21) Appl. No.: 13/694,674

(22) Filed: Dec. 21, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — C. A. Whealy

(57) ABSTRACT

A new and distinct cultivar of *Hibiscus* plant named 'Juno', characterized by its upright, mounding and uniform plant habit; freely branching habit; dense and bushy appearance; glossy dark green-colored leaves; uniformly, freely and continuous flowering habit; dark red-colored flower buds; single flowers with imbricate red purple-colored petals and dark red-colored centers; and excellent flower longevity.

3 Drawing Sheets

Botanical designation: *Hibiscus rosa-sinensis.*
Cultivar denomination: 'JUNO'.

BACKGROUND OF THE INVENTION

The present invention relates to a new and distinct cultivar of *Hibiscus* plant, botanically known as *Hibiscus rosa-sinensis*, and hereinafter referred to by the name 'Juno'.

The new *Hibiscus* plant is a product of a planned breeding program conducted by the Inventor in Sabro, Denmark. The objective of the breeding program is to create new healthy and durable *Hibiscus* plants with attractive long-lasting flowers.

The new *Hibiscus* plant originated from a cross-pollination conducted by the Inventor in October, 2007 in Sabro, Denmark of a proprietary selection of *Hibiscus rosa-sinensis* identified as code number GB-2006-1386, not patented, as the female, or seed, parent with a proprietary selection of *Hibiscus rosa-sinensis* identified as code number GB 2006-5025, not patented, as the male, or pollen, parent. The new *Hibiscus* plant was discovered and selected by the Inventor as a flowering plant within the progeny of the stated cross-pollination in a controlled greenhouse environment in Sabro, Denmark in August, 2008.

Asexual reproduction of the new *Hibiscus* plant by vegetative terminal cuttings in a controlled greenhouse environment in Sabro, Denmark since October, 2008 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Juno'. These characteristics in combination distinguish 'Juno' as a new and distinct *Hibiscus* plant:

1. Upright, mounding and uniform plant habit.
2. Freely branching habit; dense and bushy appearance.
3. Glossy dark green-colored leaves.
4. Uniformly, freely and continuous flowering habit.
5. Dark red-colored flower buds.
6. Single flowers with imbricate red purple-colored petals and dark red-colored centers.
7. Excellent flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* and the female parent selection differ in flower color as plants of the female parent selection have red-colored flowers.
2. Plants of the new *Hibiscus* and the female parent selection differ in flower shaped as plants of the female parent selection have funnelform flowers.
3. Flowers of plants of the new *Hibiscus* last about three to five days longer than flowers of plants of the female parent selection.

Plants of the new *Hibiscus* can be compared to plants of the male parent selection. Plants of the new *Hibiscus* differ primarily from plants of the male parent selection in the following characteristics:

1. Plants of the new *Hibiscus* and the male parent selection differ in flower color as plants of the male parent selection have apricot-colored flowers.
2. Plants of the new *Hibiscus* and the male parent selection differ in flower shaped as plants of the male parent selection have flowers with non-imbricate petals.
3. Flowers of plants of the new *Hibiscus* last about two to three days longer than flowers of plants of the male parent selection.

Plants of the new *Hibiscus* can be compared to plants of the *Hibiscus rosa-sinensis* 'Adonis', disclosed in U.S. Plant Pat. No. 21,592. In side-by-side comparisons conducted in Sabro, Denmark, plants of the new *Hibiscus* differed from plants of 'Adonis' in the following characteristics:

1. Plants of the new *Hibiscus* had slightly smaller flowers than plants of 'Adonis'.
2. Plants of the new *Hibiscus* and 'Adonis' differed in flower bud and flower color as plants of 'Adonis' had lighter-colored flower buds and flowers.
3. Flowers of plants of the new *Hibiscus* lasted about two to three days longer than flowers of plants of 'Adonis'.

Plants of the new *Hibiscus* can be compared to plants of the *Hibiscus rosa-sinensis* 'Boreas', disclosed in U.S. Plant Pat. No. 21,618. In side-by-side comparisons conducted in Sabro, Denmark, plants of the new *Hibiscus* differed from plants of 'Boreas' in the following characteristics:

1. Plants of the new *Hibiscus* had slightly smaller flowers than plants of 'Boreas'.
2. Plants of the new *Hibiscus* and 'Boreas' differed in flower color as plants of 'Boreas' had pale yellow-colored flowers.
3. Flowers of plants of the new *Hibiscus* lasted about one to two days longer than flowers of plants of 'Boreas'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Juno' grown in a container.

The photograph on the second sheet is a close-up view of developing flower buds and an open flower of 'Juno'.

The photograph on the third sheet is a close-up view of a dissected flower of 'Juno'.

DETAILED BOTANICAL DESCRIPTION

The aforementioned photographs and following observations, measurements and values describe plants grown during the summer in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time about eight weeks after planting and were 24 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Juno'.

Parentage:

*Female, or seed, parent*.—Proprietary selection of *Hibiscus rosa-sinensis* identified as code number GB 2006-1386, not patented.

*Male or pollen parent*.—Proprietary selection of *Hibiscus rosa-sinensis* identified as code number GB 2006-5025, not patented.

Propagation:

*Type*.—By vegetative terminal cuttings.

*Time to initiate roots, summer*.—About three weeks at temperatures of 24° C.

*Time to initiate roots, winter*.—About four weeks at temperatures of 24° C.

*Time to produce a rooted young plant, summer*.—About seven weeks at temperatures of 24° C.

*Time to produce a rooted young plant, winter*.—About eight weeks at temperatures of 24° C.

*Root description*.—Medium in thickness, fleshy; color, close to 158A.

*Rooting habit*.—Freely branching; dense.

Plant description:

*Plant and growth habit*.—Upright, mounding and uniform plant habit; moderately vigorous growth habit.

*Branching habit*.—Freely branching habit with usually about four to six lateral branches developing per plant; pinching enhances lateral branch development; dense and bushy appearance.

*Plant height*.—About 35 cm to 55 cm.

*Plant diameter* (*area of spread*).—About 30 cm to 50 cm.

Lateral branch description:

*Length*.—About 5 cm to 25 cm.

*Diameter*.—About 3 mm to 7 mm.

*Internode length*.—About 1.5 cm.

*Strength*.—Strong.

*Texture*.—Woody.

*Color, developing*.—Close to 147A.

*Color, developed*.—Close to 197A and N199A.

Foliage description:

*Arrangement*.—Alternate, single.

*Length*.—About 8 cm to 12 cm.

*Width*.—About 6 cm to 8 cm.

*Shape*.—Cordate.

*Apex*.—Acuminate.

*Base*.—Cordate.

*Margin*.—Crenate to dentate.

*Texture, upper surface*.—Smooth, glabrous; leathery.

*Texture, lower surface*.—Smooth, mostly glabrous; young leaves with scattered pubescence.

*Luster, upper surface*.—Glossy.

*Luster, lower surface*.—Matte.

*Venation pattern*.—Pinnate; arcuate.

*Color*.—Developing leaves, upper surface: Close to 137A. Developing leaves, lower surface: Close to 146A. Fully expanded leaves, upper surface: Close to N189A; venation, close to 147B. Fully expanded leaves, lower surface: Close to 147A; venation, close to 146C.

*Petiole*.—Length: About 4 cm to 6 cm. Diameter: About 2 mm. Texture, upper and lower surfaces: Pubescent. Color, upper surface: Close to 147A. Color, lower surface: Close to 143A.

Flower description:

*Flower arrangement*.—Single-type flowers arranged at terminal leaf axils; uniform, continuous and freely flowering habit with numerous flower buds and open flowers per plant at one time; flowers face mostly upright to outwardly.

*Fragrance*.—None detected.

*Natural flowering season*.—Plants flower in the garden during the spring and summer or during periods of warm weather; in the greenhouse, plants can be flowered year-round; plants begin flowering about 10 to 14 weeks after pinching.

*Flower longevity*.—Excellent flower longevity, flowers last for about five to seven days on the plant; flowers persistent.

*Flower diameter*.—About 12 cm to 15 cm.

*Flower length* (*height*).—About 8 cm to 9 cm.

*Flower buds*.—Length: About 5 cm to 7 cm. Diameter: About 2 cm to 3 cm. Shape: Obovate to elliptical. Color: Close to 53B to 53C and 1C.

*Petals*.—Arrangement: Corolla consists of five petals in a single whorl, fused at base; petals imbricate. Length: About 8 cm. Width: About 6 cm. Shape: Fan-shaped. Apex: Rounded. Base: Attenuate, fused. Margin: Entire, undulate. Texture, upper surface: Glabrous; rugose; velvety. Texture, lower surface: Glabrous; rugose; satiny. Luster, upper surface: Matte. Luster, lower surface: Slightly glossy. Color: When opening, upper surface: Between 53A and 60A; towards the base, close to 60A. When opening, lower surface: Close to 53B. Fully opened, upper surface: Close to N57A; where petals overlap, close to 58C to 58D; towards the base, close to 53A; venation, close to N57B; main color becoming closer to 61C with development. Fully opened, lower surface: Close to 53C; where petals overlap, close to 54A; venation, close to 53C.

*Sepals*.—Appearance: Five sepals fused into a tubular star-shaped calyx. Length: About 3 cm. Width: About 1.2 cm to 1.5 cm. Shape: Lanceolate. Apex: Acuminate. Margin: Entire. Texture, outer surface: Rugose, glabrous. Texture, inner surface: Smooth, glabrous. Color, outer surface: Close to 144A. Color, inner surface: Close to 143C.

*Flower bracts or epicalyx*.—Quantity per flower: About seven. Length: About 2 cm. Width: About 5 mm to 6 mm. Shape: Lanceolate. Apex: Acute. Margin: Entire. Texture, outer surface: Rugose, pubescent. Texture, inner surface: Smooth, glabrous. Color, outer and inner surfaces: Towards the base, close to 141C; towards the apex, close to 139A.

*Peduncles*.—Length: About 4 cm to 5 cm. Diameter: About 3 mm to 4 mm. Strength: Strong. Texture: Sparsely pubescent. Color: Close to 143A and 141B.

*Reproductive organs*.—Androecium: Staminal column length: About 6 cm to 7 cm. Staminal column color: Close to 58B; towards the apex, close to 58C; towards the base, close to 53A. Stamen quantity: About 100 per flower. Filament length: About 2.5 mm to 3 mm. Filament color: Close to 58B. Anther shape: Rounded to ovate. Anther length: About 1 mm to 2 mm. Anther color: Close to 19A. Amount of pollen: Abundant. Pollen grain color: Close to 17B. Gynoecium: Pistil length: About 7 cm to 8 cm. Style length: About 6 cm to 7 cm. Style texture: Smooth, waxy. Style color: Portion encased in staminal column and just above the staminal column, close to 11D; color becoming closer to 53C to 53B to 53A towards the base of the stigma pads. Stigma appearance: Five-parted, rounded, pad-like; pubescent. Stigma color: Close to 53A. Ovary color: Close to 1C.

*Seeds and fruits*.—Seed and fruit development have not been observed on plants of the new *Hibiscus*.

Temperature tolerance: Plants of the new *Hibiscus* have been observed to have tolerate temperatures from about 1° C. to about 35° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Juno' as illustrated and described.

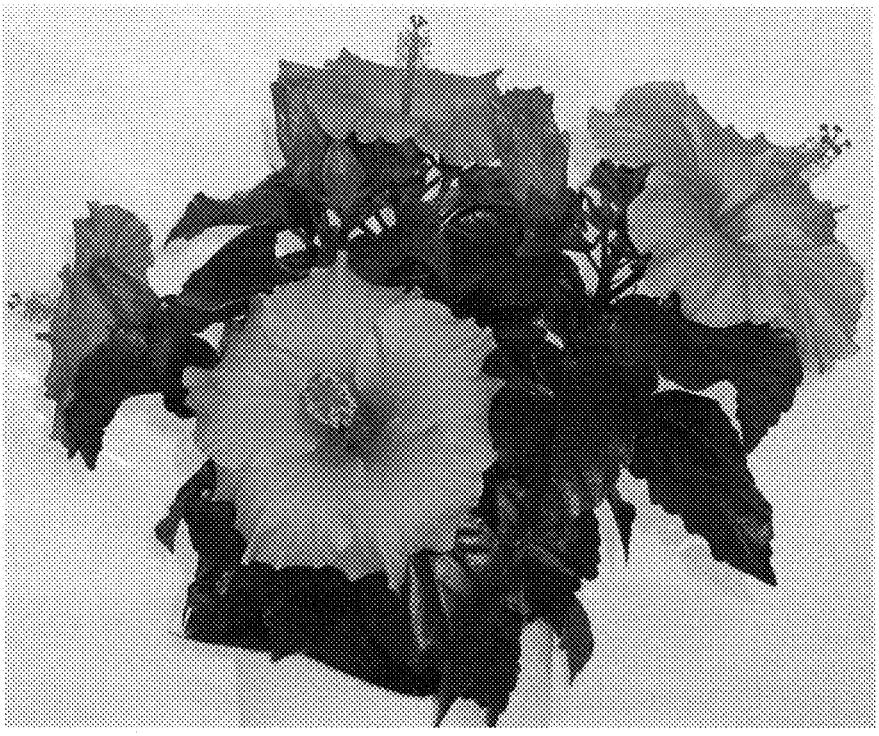

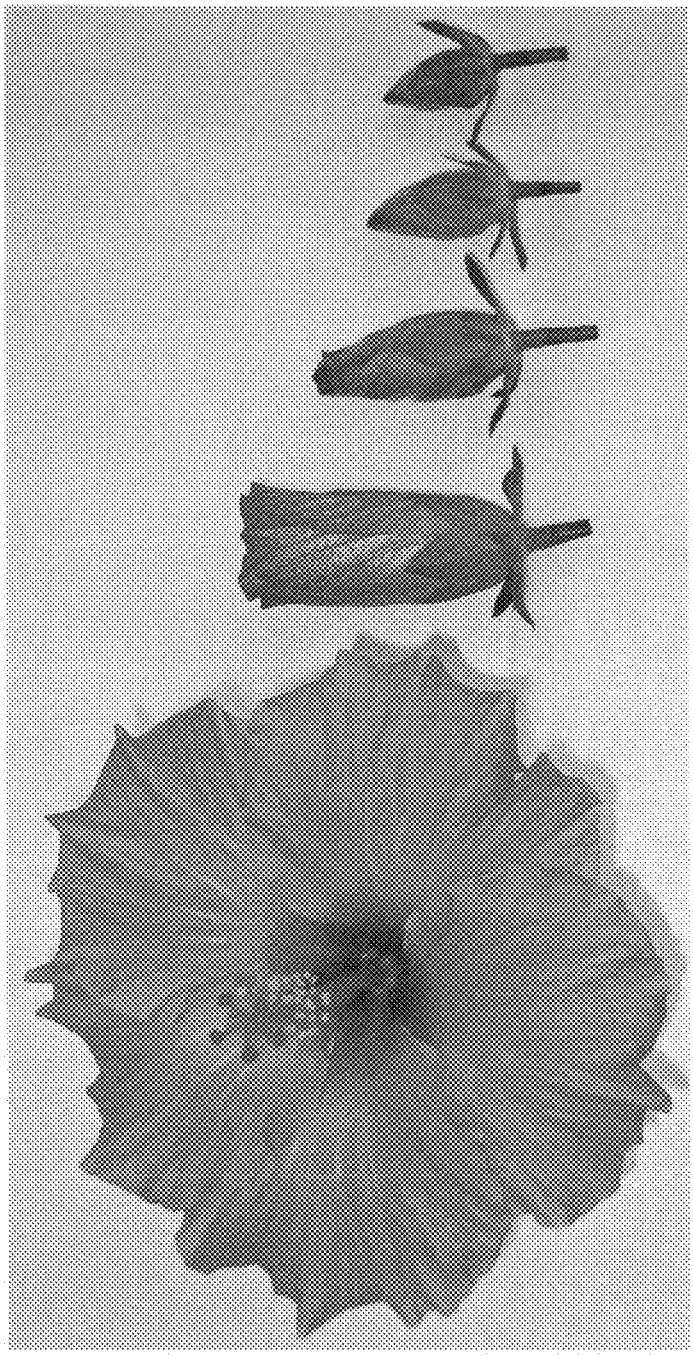

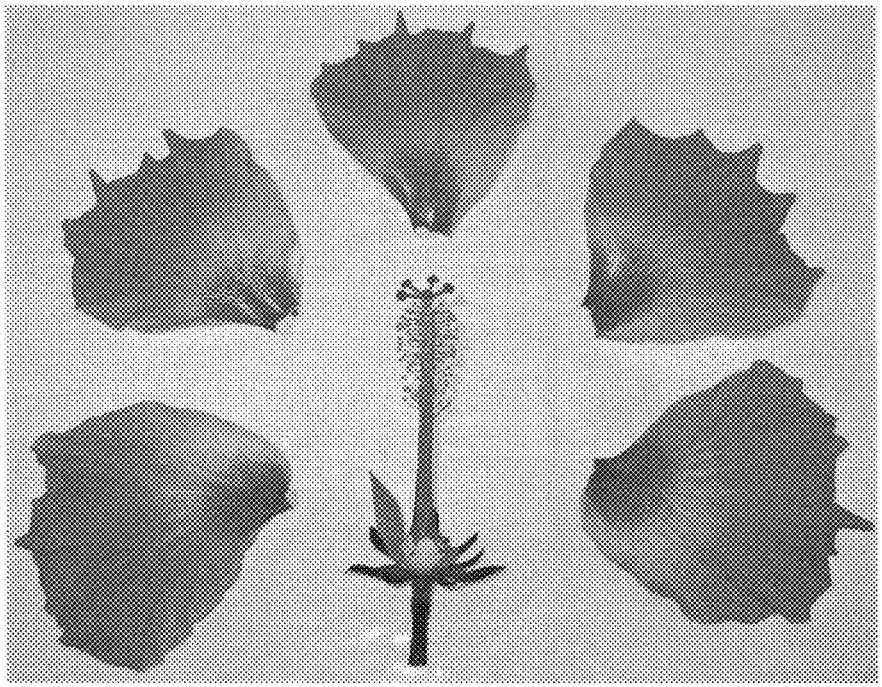

* * * * *